United States Patent [19]

Lim et al.

[11] Patent Number: 5,993,491
[45] Date of Patent: Nov. 30, 1999

[54] OXIDATIVE HAIR DYE COMPOSITIONS AND METHODS CONTAINING 1-(4-AMINOPHENYL)-2-PYRROLIDINEMETHANOLS

[75] Inventors: Mu-Ill Lim, Trumbull; Margaret Popp, Branford; Yuh-Guo Pan, Stamford, all of Conn.

[73] Assignee: Bristol-Myers Squibb Company, New York, N.Y.

[21] Appl. No.: 09/078,264

[22] Filed: May 13, 1998

[51] Int. Cl.$^6$ ........................................ A61K 7/13
[52] U.S. Cl. ........................... 8/409; 8/408; 8/423; 8/574
[58] Field of Search ............................... 8/406, 408, 409, 8/410, 411, 412, 423, 574; 548/541, 556, 566, 570, 577

[56] References Cited

U.S. PATENT DOCUMENTS

| | | | |
|---|---|---|---|
| 5,278,034 | 1/1994 | Ohki et al. | 430/444 |
| 5,538,516 | 7/1996 | Andousset et al. | 8/412 |

FOREIGN PATENT DOCUMENTS

| | | | |
|---|---|---|---|
| 0634163 | 1/1995 | European Pat. Off. | A61K 7/13 |
| 5-188549 | 7/1993 | Japan . | |
| 5-197107 | 8/1993 | Japan . | |
| 2239265 | 6/1991 | United Kingdom . | |

OTHER PUBLICATIONS

R.L.Bent et al., J.Am.Chem.Soc., Jul., 1951, vol. 73, pp. 3100–3125.

*Primary Examiner*—Yogendra Gupta
*Assistant Examiner*—Caroline D. Liott
*Attorney, Agent, or Firm*—Charles J. Zeller

[57] ABSTRACT

Compositions and methods for the oxidative coloring of human hair, wherein the compositions contain as a novel primary dye intermediate a 1-(4-aminophenyl)-2-pyrrolidinemethanol, or a cosmetically acceptable salt thereof. The compositions may also contain at least one other primary intermediate and conventional coupling compounds, in addition to an oxidizing agent and other components typically used in oxidative hair dye preparations. A preferred dye intermediate in the composition is 1-(4-aminophenyl)-2-pyrrolidinemethanol or cosmetically acceptable salts thereof, which produce intense black colors when used in admixture with a suitable coupling agents, such as 3-aminophenol, in conventional hair dye base formulations.

25 Claims, No Drawings

OXIDATIVE HAIR DYE COMPOSITIONS AND METHODS CONTAINING 1-(4-AMINOPHENYL)-2-PYRROLIDINEMETHANOLS

FIELD OF THE INVENTION

The invention relates generally to methods and compositions for preparing stable oxidative hair dyes that result in long-lasting and true colors which are different from colors produced by similar primary intermediates. The present invention more particularly relates to oxidative hair dye compositions and methods comprising 1-(4-aminophenyl)-2-pyrrolidinemethanols, as primary intermediates, in addition to other conventionally-used additives and components.

BACKGROUND OF THE INVENTION

Oxidative hair dye colorants are essential elements in hair dyeing preparations for the permanent dyeing of human hair. The hair dyeing process is achieved, in general, by the reaction of certain developing compounds with certain coupling compounds in the presence of a suitable oxidizing agent or compound, such as hydrogen peroxide.

When oxidation dyes, such as those comprising primary intermediates and couplers are used in the dyeing of human hair, the procedure may involve the use of a two part system. In general, one part can be a lotion formulation which contains a variety of ingredients, including oxidation dye precursors (i.e., primary intermediates and coupling agents). The other part is a developer formulation containing a suitable oxidizing agent, e.g., hydrogen peroxide. Immediately prior to application to the hair, the two parts are mixed to form a thickened liquid solution, for example, a lotion or a gel. As a consequence of the oxidizing properties of the oxidizing agent, some of the natural melanin pigment of the hair may be bleached. The precursors in the thickened solution (e.g. lotion or gel) penetrate into the hair where the primary intermediates are oxidized and react with the coupling agents to produce the desired color. Such systems generally contain a proportion of organic solvents and surfactants and contain relatively high levels of dye precursors to produce the desired color.

In order for procedures using permanent oxidative dyes to work properly, a number of parameters and conditions are important to consider in the use of these dyes in admixture with couplers in hair color preparations for human hair. Among these are the final color and color intensity that are produced after application to the subject's hair; the wash fastness and the light fastness of the resulting dye; the resistance of the dye to perspiration; the resistance of the dye to various hair treatments, such as permanent wave, straightening, shampooing, conditioning and rubbing. In addition, the dye must have virtually no allergenicity or dermal or systemic toxicity.

p-Phenylenediamine plays a very important role in oxidative hair coloring because a majority of shades are obtained with dyes based on this dye. However, the hair coloring industry is searching for p-phenylenediamine alternatives possessing better allergenic profiles than p-phenylenediamine. As part of the solution, GB 2,239,265A describes that 2-(2-hydroxyethyl)-p-phenylenediamine can be used as a potential replacement for p-phenylenediamine. U.S. Pat. No. 5,538,516 also describes the use of 2-(hydroxyalkoxy)-p-phenylenediamine as a p-phenylenediamine substitute. European patent 634,163A lists more than 40 compounds of p-phenylenediamine derivatives. Among them, N-4-aminophenylmorpholine and N-4-aminophenylpiperidine were described. Morpholine and piperidine derivatives are examples of heterocyclic compounds. No example of pyrrolidine was found in the list. However, these compounds are not good primary intermediates because the energy required for the formation of the oxidized forms of the piperidine and morpholine derivative is higher than for the open chain compound such as 4-amino-N,N-diethylaniline (R. L. Bent, J. C. Desslock, F. C. Duennbier, D. W. Fassett, D. B. Glass, T. H. James, D. B. Julian, W. R. Ruby, J. M. Snell, J. H. Sterner, J. R. Thirtle, P. W. Vittum and A. Weissberger, J. Am. Chem. Soc. 1951, 73, 1300). It was also reported in this paper that formation of the oxidized compound is even more favorable for 1-(4-aminophenyl) pyrrolidine than for the 4-aminodialkylanilines with open alkyl groups such as 4-amino-N,N-diethylaniline. Although 1-(4-aminophenyl)pyrrolidine has a good potential as a primary intermediate, it was found to exhibit a strong allergenic activity. Because of adverse biological activity and various limitations, there is need for developing pyrrolidine derivatives which can be used as p-phenylenediamine alternatives.

In R. L. Bent, J. C. Dessloch, F. C. Duennbier, D. W. Fassett, D. B. Glass, T. H. James, D. B. Julian, W. R. Ruby, J. M. Snell, J. H. Sterner, J. R. Thirtle, P. W. Vitt, A. Weissberger, Chemical constitution, Electrochemical, Photographic and allergenic properties of p-amino-N-dialkyanilines, J. Am. Chem. Soc. 1951, 73, 1300, a total of 60 of 4-amino-N, N-dialkylanilines were studied on allergenic properties. 1-(4-Aminophenyl)pyrrolidine was one of them mentioned in the studies.

SUMMARY OF THE INVENTION

It is an object of the invention to provide oxidative hair dye compositions and methods for the oxidative coloration of hair comprising compounds of the class of 1-(4-aminophenyl)-2-pyrrolidinemethanols, or cosmetically acceptable salts thereof, as primary intermediates in compositions comprising such primary dye intermediates as well as coupling agents, oxidizing agents and other adjuvant substances. In accordance with a particular aspect of the invention 1-(4-aminophenyl)-2-pyrrolidinemethanol is preferred.

It is a further object of the invention to provide 1-(4-aminophenyl)-2-pyrrolidinemethanol compounds that serve as effective and high-performance primary intermediates in oxidative hair dyes. The 1-(4-aminophenyl)-2-pyrrolidinemethanol compounds of the invention are capable of replacing, in whole or in part, p-phenylenediamine (PPD), a known allergen and a sensitizer, and can be employed with couplers as color modifiers in such hair dye formulations.

Yet another object of the invention is to provide a newly-discovered primary dye intermediate, 1-(4-aminophenyl)-2-pyrrolidinemethanol, or a cosmetically acceptable salt thereof, which provides intense color when used in oxidative hair dye compositions in combination with coupling agents, oxidizing agents and other hair dye additives and/or adjuvants conventionally used in hair dye formulations for the dyeing of hair.

Further objects and advantages afforded by the invention will be apparent from the detailed description hereinbelow.

DETAILED DESCRIPTION OF THE INVENTION

The present invention provides novel compounds which are primary intermediates for use in oxidative hair dye compositions. The compositions of the present invention include, as primary dye intermediates, one or more components from the chemical class of substituted or unsubstituted 1-(4-aminophenyl)-2-pyrrolidinemethanol compounds and cosmetically acceptable salts thereof. Nonlimiting examples of derivatives and salts of the 1-(4-aminophenyl)-2-pyrrolidinemethanol compounds include sulfates, hydrochlorides, phosphates and the like, with sulfates being preferred. The 1-(4-aminophenyl) pyrrolidine compounds of the present invention are generally represented by the following chemical formula I:

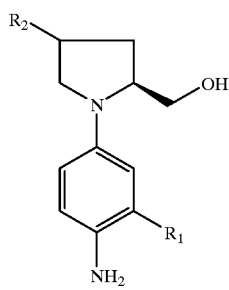

I wherein $R_1$ is a hydrogen; $C_1$–$C_6$ alkyl, preferably $C_1$–$C_4$ alkyl; or $C_1$–$C_5$ mono- or polyhydroxyalkyl, preferably $C_1$–$C_3$ mono- or polyhydroxyalkyl, and $R_2$ is hydrogen or hydroxyl group. Preferred are unsubstituted 1-(4-aminophenyl)-2-pyrrolidinemethanol (e.g., formula I, wherein $R_1$ and $R_2$ are hydrogen), as well as substituted 1-(4-aminophenyl)-2-pyrrolidinemethanols (e.g., formula I, wherein $R_1$ is methyl or ethyl and $R_2$ is hydrogen), and 1-(4-aminophenyl)-4-hydroxy-2-pyrrolidinemethanol (e.g., formula I, where $R_1$ is hydrogen and $R_2$ is hydroxyl group).

The compositions of the present invention contain as a primary dye intermediate one or more substituted or unsubstituted 1-(4-aminophenyl)-2-pyrrolidinemethanol compounds, or a cosmetically acceptable salt thereof, which may be present in admixture with one or more other oxidation dye precursor(s), for example, primary dye intermediate or conventional coupling component(s), in addition to other hair dye component ingredients, additives, or adjuvants typically used in oxidative hair dye formulations as described herein. The 1-(4-aminophenyl)-2-pyrrolidinemethanol, alone or in combination with one or more other dye intermediates and coupling agents produce novel dyestuffs which provide intense coloration to hair. The 1-(4-aminophenyl)-2-pyrrolidinemethanol compounds of the present invention achieve a deep coloration to hair and impart unique properties to dye substances used for oxidative hair coloring.

The compounds of the present invention, which are of the class of 1-(4-aminophenyl)-2-pyrrolidinemethanols, or cosmetically acceptable salts thereof, are distinct from hair dyeing compounds disclosed in the prior art and offer newly-discovered and advantageous hair coloring properties.

It will be appreciated by those having skill in the art that the compositions and methods of the present invention are appropriate for the dyeing of keratinous fibers, including the hair fibers of animals and humans, with particular application to the oxidative coloring of human hair.

It has been found surprisingly that dyes produced by coupling the compound 1 or 1a with conventional couplers are different from those derived from coupling 1-(4-aminophenyl)pyrrolidine 2 or N,N-bis(2-hydroxyethyl)-p-phenylenediamine 3 with the same couplers in spite of the fact that the compounds are structurally similar to each other.

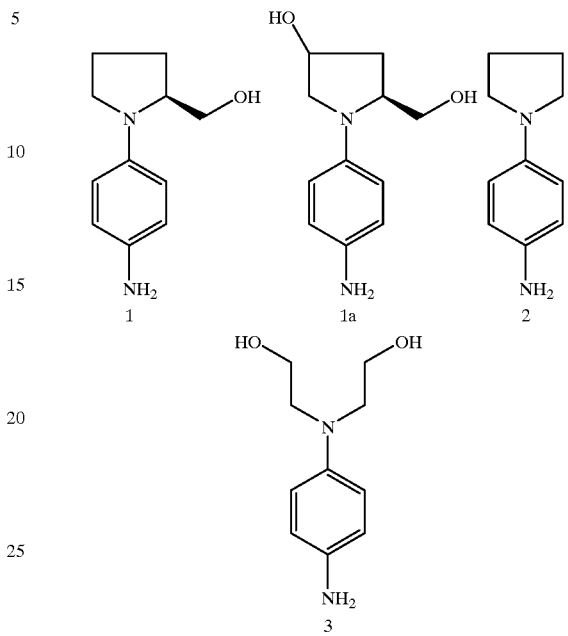

For example, 1-(4-aminophenyl)-2-pyrrolidinemethanol (1) couples with 3-methyl-1-phenyl-2-pyrazolin-5-one to produce a dye which colors piedmont hair intense dark violet. The compound of formula 1a also produces violet when coupled with 3-methyl-1-phenyl-2-pyrazolin-5-one. In contrast, 1-(4-aminophenyl)pyrrolidine (2) couples with 3-methyl-1-phenyl-2-pyrazolin-5-one to produce a dye which imparts a reddish violet coloration to piedmont hair. N,N-bis(2-hydroxyethy)-p-phenylenediamine (3) imparts blue violet coloration to piedmont hair. These visual differences are well manifested in the CIE L*a*b* values (compare entries 1, 7 and 12 in Table 2). In the chromaticity diagram, -b* is the blue direction.

2,4-Diaminophenoxyethanol couples with the novel primary intermediate of the present invention to produce a dye which colors piedmont hair intense blue. The blue color obtained is different from that derived from 1-(4-aminophenyl)pyrrolidine 2 and 2,4-diaminophenoxyethanol. b* Value of the former is -12.98, while the latter b* is -9.36 (Table 2). The dye on gray hair exhibits excellent wash and light fastness (Table 5).

2-Methyl-1-naphthol couples with 1 to impart a blue color on piedmont hair. Again, the compound 1 provides a b* value -20.3 which is substantially lower than the counterpart b* value -13.07 obtained with the compound 2.

3-Aminophenol couples with 1 to produce a dye which colors hair dark black, while compound 2 colors hair neutral black. The color on gray hair exhibits excellent wash and light fastness properties (Table 4).

Overall wash and light fastness of 1 is better than those of N,N-bis(2-hydroxyethyl)-p-phenylenediamine 3 when coupled with m-aminophenol or 2,4-diaminophenoxyethanol as shown in Table 4 and 5. The smaller ΔE is, the better wash and light fastness is.

Violet color obtained from 1 and 3-methyl-1-phenyl-2-pyrazolin-5-one is very similar to that produced from p-phenylenediamine and 2-methyl-5-aminophenol (see entries 1 and 13 in Table 2). This observation may allow one to formulate a red shade without relying on p-phenylenediamine. The red shade is generally produced by a combination of p-phenylenediamine, p-aminophenol and 2-methyl-5-aminophenol.

As described above, in addition to at least one of the novel component dye molecules encompassed by the present invention, the hair dyeing compositions described herein may also contain at least one other known and usual oxidation dye precursor (i.e., used as primary dye intermediates and/or couplers), as well as conventional direct colorants and dyes in admixture, should these substances be necessary or desired for the development and production of certain color nuances and tints.

Illustrative component dye ingredients that are conventionally admixed and employed as constituents of customary hair dye formulations and that can be considered suitable for use in the compositions of the present invention are set forth hereinbelow. As one particular example, p-phenylenediamine, used in oxidative hair coloring formulations, may conveniently be used in admixture with the novel primary intermediate 1-(4-aminophenyl)-2-pyrrolidinemethanol compounds in the compositions of the present invention.

Included among the suitable dye components that may be considered for use as primary intermediates and/or couplers in the dye compositions of the present invention are the following: p-phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N, N-bis-(2-hydroxyethyl)-N, N-bis (4-aminophenyl)-2-propanol; and 2-methyl-4-dimethylaminoaniline, or combinations thereof.

Preferred p-phenylenediamine derivatives include: p-toluenediamine; p-phenylenediamine; N-2-methoxyethyl-p-phenylenediamine; N,N-bis(hydroxyethyl)-p-phenylenediamine; and 2-hydroxyethyl-p-phenylenediamine.

p-Aminophenol derivatives include: p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid, or combinations thereof.

Preferred p-aminophenol derivatives include: p-aminophenol; p-methylaminophenol; 3-methyl-p-aminophenol; 2-methyl-p-aminophenol; 2-(2-hydroxyethylaminomethyl)-p-aminophenol; 2-methoxymethyl-p-aminophenol; and 5-aminosalicylic acid.

Ortho developers include: catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol, or combinations thereof.

Preferred ortho developers include: o-aminophenol; 2,4-diaminophenol; 2,4,5-trihydroxytoluene; 1,2,4-trihydroxybenzene; 2-ethylamino-p-cresol; 5-methyl-o-aminophenol; 6-methyl-o-aminophenol; and 2-amino-5-acetaminophenol.

Phenols, naphthols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid, or combinations thereof.

Preferred phenols, naphthols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; thymol (2-isopropyl-5-methylphenol); and 2,3-dihydroxy-1,4-naphthoquinone.

m-Phenylenediamines include: m-phenylenediamine; 2-(2,4-diaminophenoxy)ethanol; N,N-bis(hydroxyethyl)-m-phenylenediamine; 2,6-diaminotoluene; N,N-bis (hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene, or combinations thereof.

Preferred m-phenylenediamines include: m-phenylenediamine; 2,4-diaminophenoxyethanol; bis-(2, 4-diaminophenoxy)-1,3-propane; 1-hydroxyethyl-2,4-diaminobenzene; 2-amino-4-hydroxyethylaminoanisole; 4,6-bis(hydroxyethoxy)-m-phenylenediamine; 2,4-diamino-5-methylphenetole; 2,4-diamino-5-hydroxyethoxytoluene; 2,4-dimethoxy-1,3-diaminobenzene; and 2,6-bis (hydroxyethylamino)toluene.

m-Aminophenols include: m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol, or combinations thereof.

Preferred m-aminophenols include: m-aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol.

Heterocyclic derivatives include: 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4-hydroxyindole; 3-amino-5-hydroxy-2,6-dimethoxypyridine; 5,6- dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Preferred heterocyclic derivatives include: 4,5-diamino-1-methylpyrazole; 2-dimethylamino-5-aminopyridine; 2,4,5,6-tetra-aminopyrimidine; 1-phenyl-3-methyl-5-pyrazolone; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 4-hydroxyindole; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine.

Particularly preferred couplers for use in combination with the compounds of the present invention are resorcinol, m-aminophenol, 2,4-diaminophenoxyethanol and 2-methyl-1-naphthol, which may be used alone or in combinations of two or more. The most preferred compositions of the present invention comprise 1-(4-aminophenyl)-2-pyrrolidinemethanol 1 and/or N-(4-aminophenyl)-4-hydroxy-2-pyrrolidinemethanol 1a in combination with a coupler or coupler system selected from:

(a) m-aminophenol;

(b) resorcinol;

(c) m-aminophenol and resorcinol;

(d) resorcinol and 2,4-diaminophenoxyethanol;

(e) m-aminophenol and 2-methyl-1-naphthol;

(f) 2,4-diaminophenoxyethanol and m-aminophenol, and (g) resorcinol and 2-methyl-1-naphthol.

These combinations produce in combination with Compounds 1 and 1a neutral black, dark black and blue black shades.

The 1-(4-aminophenyl)-2-pyrrolidinemethanol primary intermediate is present in the compositions of the present invention in an amount of about 0.01 to 10% by weight, preferably about 0.1 to 5%, based on the total weight of the composition.

The additional dye compounds, e.g., couplers, should be present in the hair dyeing compositions of the present invention in an amount of approximately 0.01 to 10%, by weight, preferably approximately 0.1 to 5%, by weight, based on the total weight of the composition. The total quantity of oxidative colorant, comprising primary intermediate(s) and coupler(s), will suitably amount to approximately 0.1 to 10%, by weight, and preferably, approximately 0.5 to 5% by weight, based on the total weight of the composition.

Unless indicated otherwise, as used herein, reagent or component amounts are in % by weight (w/w), based on the total weight of the composition.

In the compositions of the present invention, the coupling component is generally used in approximately equimolar amounts relative to the primary intermediate (developing component). However, it will be appreciated that the primary intermediate in relation to the coupler, may be present either in increased or decreased amounts depending upon the formulation and the desired color, intensity or effect. In general terms, the primary intermediate and the coupling component, or cosmetically acceptable salts thereof, will be present in tinctorially effective amounts for the coloring of a hair fiber.

The hair dye preparations of the present invention may be formulated into cosmetic preparations such as a solution, cream, lotion, gel or emulsion. Also, in accordance with the invention, the compositions may represent a mixture of the coloring components (i.e., dye intermediate and coupling agent) with other components commonly associated with the formulation of solutions, creams, lotions, gels or emulsions, and the like. For example, components such as wetting agents or emulsifying agents from the categories of anionic or nonionic surfactants, such as sulfates of fatty alcohols, alkanolamides of fatty alcohols, alkyl sulfonates, alkylbenzene sulfonates, oxyethylated fatty alcohols, oxyethylated nonylphenols; furthermore thickeners such a fatty alcohols, starch, cellulose derivatives, paraffin oil and fatty acids, as well as hair-care substances such as lanolin derivatives, cholesterol and pantothenic acid, may be formulated into the compositions of the invention.

As an example, if formulated as a lotion, the compositions of the invention may contain organic solvents to assist in dissolving the dye precursors. Accordingly, the organic solvent content of the lotion may be from 0% to about 20%, preferably, about 1% to about 15%. Typically useful solvents include alcohols containing up to three carbon atoms such as ethanol and isopropanol, polyhydroxy alcohols such as propylene or hexylene glycol and lower alkyl ethers thereof, such as ethoxy ethers.

In addition, the hair dyeing compositions in accordance with the present invention may optionally contain conventionally-used adjuvants and cosmetic additives, or mixtures thereof, to achieve the final formulations. Examples of such additives include, but are not limited to, anti-oxidants, e.g., ascorbic acid, erythorbic acid, or sodium sulfite, to inhibit premature oxidizing; fragrances and/or perfume oils; chelating agents; emulsifiers; coloring agents; thickeners; organic solvents; opacifying agents; dispersing agents; sequestering agents; hair-care substances; humectants; and antimicrobials, and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, *Cosmetics: Science and Technology*, Vol. 2, Second Edition, (1972).

Thickeners that may be used in the compositions of the present invention include a variety of fatty acid soaps and associative polymeric thickeners. The fatty acid soaps are alkaline metal salts or alkanolamine salts of fatty acids with $C_{10}$–$C_{16}$ alkyl side chains. The preferred fatty acids include oleic acid, myristic acid and lauric acid, which are generally present in the compositions of the invention at about 0.5% to about 20%, preferably about 1% to about 10%. Associative thickeners are polymers that can thicken solutions at low concentrations. Among the associative thickeners that are useful in the compositions of the present invention are acrylates copolymer (sold by Rohm and Haas under the tradename Aculyn-33), ceteareth-20 acrylates/steareth-20 methacrylate copolymer (sold by Rohm and Haas under the Trade Name Aculyn-22), acrylates/steareth-20 itaconate copolymer and acrylates/ceteth-20 itaconate copolymer. Another class of associative thickeners useful in the compositions of the present invention include the copolymers of polyurethane and polyethylene glycol or polyether urethanes. One such material is sold by Rohm and Haas under the tradename Aculyn-44. The associative polymeric thickeners are generally present in the compositions of the invention at about 0.1% to about 10%, preferably, about 0.5% to about 5%.

The oxidative coupling, i.e., the development of the dye, to produce the final color product on the hair, can, in principle, be performed with atmospheric oxygen. However, chemical oxidizing agents are suitably and preferably used. Although other oxidizing agents can be employed, hydrogen peroxide is a preferred oxidizing compound for use as a developer with the primary intermediate and coupler dye precursors of the invention. The concentration of hydrogen peroxide in the developer may be from about 1% to about 15%, preferably, from about 3% to about 12%. Other suitable oxidizing agents include, for example, urea peroxide, melamine peroxide, perborates and percarbonates such as sodium perborate or percarbonate. The amounts of such oxidizing agents can be routinely determined by one having skill in the art, without requiring any inventive skill.

The compositions of the invention may include a typical anionic, cationic, nonionic or amphoteric surfactant. The anionic surfactants include the variety of alkyl sulfates, alkylether sulfates, alkyl sulfonates, alkyl sulfosuccinates and N-acyl sarcosinates. The commonly used anionic surfactants are sodium and ammonium lauryl sulfates, sodium and ammonium laureth sulfate and alpha olefin sulfonates. Anionic surfactants are generally present in the compositions of the present invention at about 0.1% to about 15%, preferably, about 0.5% to about 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauroyl diethanolamide; lauroyl monoethanolamide; isopropyl palmitate, isopropyl stearate and decylpolyglucoside. Nonionic surfactants are generally present in the compositions of the present invention at about 0.1% to about 15%, preferably, about 0.5% to about 10%.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to about 10%, preferably, about 0.5% to about 5%.

Amphoteric surfactants that can be incorporated in the compositions of the present invention belong to the class of surface active chemicals that possess a positive and a negative charge in the same molecule and behave as a cation, an anion, or both, depending upon the pH of the medium and the nature of the amphoteric molecule. In general, the positive charge is located on a nitrogen, while the negative charge is carried by a carboxyl or sulfonate group. There are a large number of amphoteric surfactants that are suitable for use in the present invention, including, for example, the well-known betaines, sultaines, glycinates and propionates.

The selection of the amphoteric surfactant or mixture of surfactants for use in the present compositions and methods is not critical. The surfactant may be selected from among those suggested above, or from any of a number of other known amphoteric surfactants. The amount of amphoteric surfactant in the compositions of the present invention is normally from about 0.5% to about 15%, preferably, about 2% to about 10%.

Depending on the final formulated preparation, the compositions in accordance with invention may be weakly acidic, neutral or alkaline. In particular, the pH of the prepared compositions can range from about 5 to about 11. Preferred is a pH range of about 8 to 10. Any of a wide variety of alkaline reagents can be used to adjust the pH of the hair coloring compositions. Such alkaline reagents include ammonium hydroxide, potassium or calcium hydroxide, sodium or potassium carbonate, sodium phosphate, sodium silicate, guanidine hydroxide, or any one of the alkylamines or alkanolamines, for example, ethylamine, triethylamine, trihydroxymethylamine, ethanolamine, diethanolamine, aminomethyl propanol, aminomethyl propanediol and the like. The preferred alkaline reagents are ammonium hydroxide, sodium carbonate and ethanolamine. With the reagents listed above, the selected pH will generally be achieved if the composition contains an alkaline agent in an amount from about 0.1% to about 15%, preferably, about 0.5% to about 5%.

The application of the dyeing components is carried out by methods familiar to those in the art, for example, by mixing the hair dyeing preparation with an oxidant shortly before use, or at the time of applying the mixture onto the hair. On the hair, the compositions form a stable formulation with enough consistency and body to remain on the hair without dripping or running during the complete coloring period. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 5 to 45 minutes, preferably, approximately 10 to 30 minutes), the composition is washed from the hair with an ordinary water rinse followed by a shampoo. The application temperature is in the range of about 15° C. to 50° C.

The 1-(4-aminophenyl) pyrrolidine methanols and cosmetically-acceptable derivatives and salts thereof, are soluble in water and have a long shelf life, particularly as constituents of the hair dyeing preparations in accordance with the invention. These primary intermediates, of which 1-(4-aminophenyl)-2-pyrrolidinemethanol is preferred, should be present in the hair dyeing preparations in an amount of approximately 0.1% to approximately 10%, preferably, approximately 0.1% to approximately 5%. The total quantity of oxidative colorant, consisting of primary intermediate(s) and coupling component(s) will suitably amount to approximately 0.1% to approximately 20%, and preferably, approximately 0.5% to approximately 15% of the composition.

The hair dyeing compounds in accordance with the invention will offer a wide range of varying color tints depending upon the type and composition of the colorant constituents. The color tints are distinguished herein by their particular intense and lasting color. The superior coloring properties of the hair dyeing compositions of the present invention are further evidenced by allowing grayed hair that has not been subjected to prior chemical damage to be covered without problems and with a depth and covering strength that, prior to the discovery of the primary intermediates of the present invention, had only been attained using the conventional PPD.

The compositions of this invention may be separately provided in a kit or packaged form ready for mixing by the user, either professional or consumer, to initiate the dyeing process. The kit provided in accordance with this invention comprises containers for housing the developer and the dye precursors. In the most convenient form, there will be two containers, one containing the primary dye intermediate and coupler, e.g., as a lotion; the other containing the oxidizing agent, also called the developer or developing agent.

The method of the invention comprises applying the mixture to the hair to be colored and allowing it to remain in contact with the hair until the desired hair color has been attained, after which time the composition is removed from the hair as described above.

EXAMPLES

The examples as set forth herein are meant to exemplify the various aspects of carrying out the invention and are not intended to limit the invention in any way.

Example 1

The Synthesis of Compound 1

1-Flouro-4-nitrobenzene 4 (13.3 g, 94 mmole) is treated with (s)-(+)-2-pyrrolidinemethanol 5 (9.5 g, 94 mmole) and potassium carbonate (15.6 g, 113 mmole) in DMF (188 ml, 0.5M solution) at 60° C. for 6 hours. The reaction is cooled to room temperature. The solvent is evaporated under vacuum and the residue is taken up into dichloromethane (500 ml). The organic phase is washed with saturated NaCl solution (250 ml). The phases are separated and the organic phase is dried over $MgSO_4$, filtered, and evaporated under vacuum to leave an orange oil. The crude material is then crystallized from ethyl acetate/hexane to produce compound 6 (18.3 g, 88% yield) as a bright yellow solid: mp 118–120° C.; $^1$H NMR (300 MHz, DMSO-$d_6$) δ 2.06 (m, 4H), 3.31 (m, 2H), 3.55 (d, 2H, J=9.0 Hz), 3.98 (s, 1H), 4.97 (t, 1H, J=6.0 Hz), 6.77 (d, 2H, J=8.7 Hz), 8.12 (d, 2H, J=8.7 Hz); m/z 222 ($M^+$).

Compound 6 (13.3 g. 60 mmole) is then hydrogenated at 60 psi of hydrogen in the presence of 10% Pd on carbon (1.3 g) in ethanol (222 ml, 0.27M solution) for 2 hours at room temperature. The solution is then filtered through a pad of Celite, evaporated, and the crude material is recrystallized from ethyl acetate/hexane to give compound 1 (10.1 g, 88% yield) as a light grey solid: mp 94–95° C.; $^1$H NMR (300 MHz, DMSO-$d_6$) δ 1.86 (m, 4H), 2.84 (m, 1H), 3.11 (m, 1H), 3.29 (m, 3H), 4.29 (bs, 2H), 4.66 (bs, 1H), 6.38 (d, 2H, J=8.1 Hz), 6.48 (d, 2H, J=8.1 Hz); m/z 192 ($m^+$).

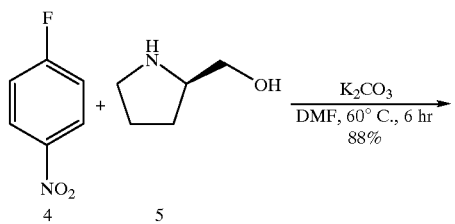

4  5

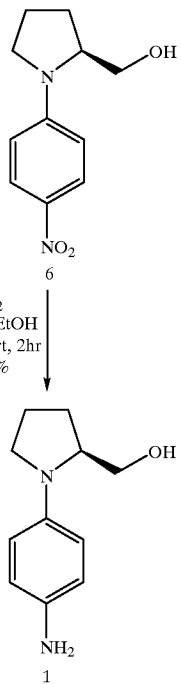

Example 2

The Synthesis of Compound 1a

1-Fluoro-4-nitrobenzene 4 (42.3 g, 0.3 mole) is treated with trans-4-hydroxy-L-proline 7 (39.3 g, 0.3 mole) in the presence of potassium fluoride (17.4 g, 0.3 mole) and 18-Crown-6 (6.1 g, 30.0 mmole) in DMSO (300 ml) at 60° C. for 18 hours. The reaction is cooled to room temperature and poured into an ice chilled saturated NaCl solution (500 ml). The resulting aqueous solution is acidified to pH about 3 with aqueous 10% HCl. The aqueous phase is extracted with EtOAc (3×500 ml). The organic phases are combined, dried over $MgSO_4$, and the solvent is vacuum evaporated. The crude material is then recrystallized from EtOAc/hexane to afford compound 8 (71.1 g, 94% yield) as a dark yellow solid: mp 98–100° C.; $^1$H NMR (300 MHz, DMSO-$d_6$) δ 2.18–2.28 (m, 2H), 3.32 (dd, 1H, J=10.0, 2.1 Hz), 3.65 (dd, 1H, J=11.0, 5.0 Hz), 4.43 (m, 2H), 5.31 (s, 1H), 6.62 (d, 2H, J=9.0 Hz), 8.12 (d, 2H, J=9.0 Hz), 13.10 (bs, 1H); m/z 252 ($M^+$).

Compound 8 (31.5 g, 125 mmole) is then reduced with 1.0M $BH_3$-THF complex (375 ml, 375 mmole) in THF (125 ml) at room temperature overnight (18 hrs). The excess $BH_3$-THF complex is quenched with the slow addition of MeOH (100 ml). The solvent is then vacuum evaporated. The residue is taken up into EtOAc (500 ml) and an ice chilled saturated NaCl solution (500 ml). The aqueous phase is extracted with EtOAc (3×500 ml). EtOH (50 ml) is added due to solubility problems. The organic phases are combined, dried over $MgSO_4$, and the solvent is vacuum evaporated. The crude material is recrystallized from EtOAc/hexane to give compound 9 (13.0 g, 44% yield) as a yellow solid: mp 155–157° C.; $^1$H NMR (300 MHz, DMSO-$d_6$) δ 1.96–2.03 (m, 1H), 2.56 (m, 1H), 3.18 (dd, 1H, J=10, 7.4 Hz), 3.50 (t, 2H, J=5.1 Hz), 3.68 (dd, 1H, J=11, 6 Hz), 4.09 (m, 1H), 4.55 (m, 1H), 4.90 (t, 1H, J=5.7 Hz), 5.14 (d, 1H, J=4.5 Hz), 6.73 (d, 2H, J=9.3 Hz), 8.08 (d, 2H, J=9.3 Hz); m/z 238 ($M^+$).

Compound 9 (10.0 g, 42.0 mmole) is then hydrogenated at 60 psi of hydrogen in the presence of 10% Pd on carbon (1.5 g) in ethanol (200 ml, 0.2M solution) for 6 hours at room temperature. The solution is vacuum filtered through a pad of celite and the solvent is vacuum evaporated. The crude material is recrystallized from EtOAc/hexane to give compound 1a (6.7 g, 75% yield) as a light tan solid: mp 130–132° C.; $^1$H NMR (300 MHz, DMSO-$d_6$) d 1.74 (m, 1H), 2.02 (m, 1H), 2.67 (m, 1H), 3.09 (m, 1H), 3.39 (m, 1H), 3.49 (m, 1H), 4.20 (m, 2H), 4.31 (m, 1H), 4.55 (m, 1H), 4.81 (m, 1H), 6.28 (d, 2H, J=7.8 Hz), 6.41 (d, 2H, J=7.8 Hz); m/z 208 (M$^+$).

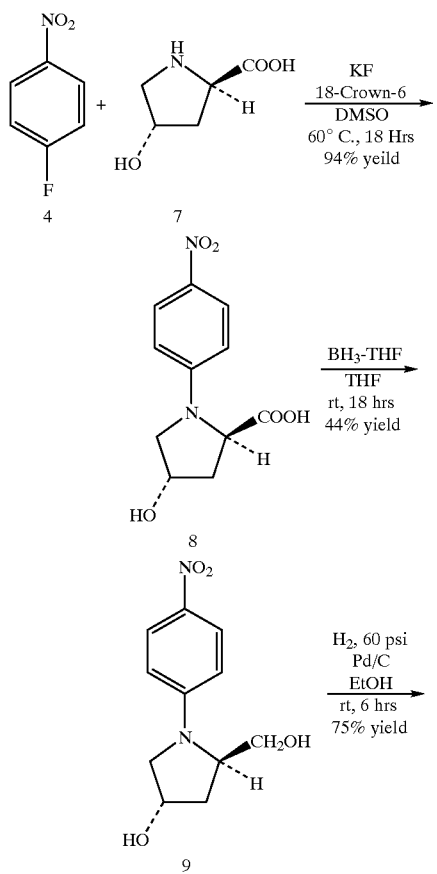

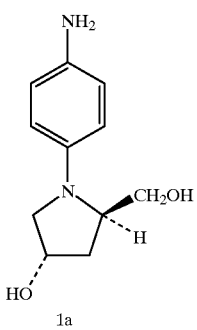

1a

2. Dyeing Procedure

The following compositions (1 or 1a or 2 or 3 or ppd and coupler: 5 mmole each) shown in table 1 are mixed with 100 g of 20 volume hydrogen peroxide. The resulting mixture is applied to piedmont hair or gray hair and permitted to remain in contact with hair for 30 minutes. Thus dyed hair is then shampooed and rinsed with water and dried. Table 2 shows the CIE L*a*b* values and colors obtained on piedmont hair.

TABLE 1

Dyeing Composition

| | Composition (%) |
|---|---|
| Cocamidopropyl betaine | 17 |
| Ethanolamine | 2 |
| Oleic Acid | 0.75 |
| Citric Acid | 0.1 |
| Ammonium hydroxide | 5.0 |
| Behentrimonium chloride | 0.5 |
| Sodium sulfite | 0.1 |
| EDTA | 0.1 |
| Erythorbic acid | 0.4 |
| Primary intermediate (1, 1a, 2, 3 or ppd) | 5 mmole |
| Coupler | 5 mmole |
| Water | QS 100 |

TABLE 2

Colors Obtained from Coupling of 1, 1a, 2, 3 or PPD with Various Couplers on Piedmont Hair

| Entry No. | PI | Coupler | L* | a* | b* | Color Description |
|---|---|---|---|---|---|---|
| 1 | 1 | 3-Methyl-1-phenyl-2-pyrazolin-5-one | 23.48 | 12.77 | −1.09 | intense violet |
| 2 | 1a | 3-Methyl-1-phenyl-2-pyrazolin-5-one | 27.18 | 12.63 | −4.83 | Violet |
| 3 | 1 | 2,4-Diaminophenoxyethanol | 18.99 | 3.05 | −12.98 | Blue |
| 4 | 1 | 2-Methyl-1-naphthol | 21.33 | 6.16 | −20.3 | Blue |
| 5 | 1 | 3-Aminophenol | 21.06 | 0.22 | −6.75 | Black |
| 6 | 1 | 2-Amino-3-hydroxypyridine | 19.90 | 3.20 | −3.90 | Blue violet |
| 7 | 2 | 3-Methyl-1-phenyl-2-pyrazolin-5-one | 28.73 | 16.10 | 4.39 | reddish violet |
| 8 | 2 | 2,4-Diaminophenoxyethanol | 18.27 | 2.47 | −9.36 | Blue |
| 9 | 2 | 2-Methyl-1-naphthol | 20.69 | 4.81 | −13.07 | Blue |
| 10 | 2 | 3-Aminophenol | 18.82 | 0.09 | −3.71 | Neutral black |
| 11 | 2 | 2-Amino-3-hydroxypyridine | 19.44 | 1.90 | −1.62 | Dark brown |

TABLE 2-continued

Colors Obtained from Coupling of 1, 1a, 2, 3 or PPD with Various Couplers on Piedmont Hair

| Entry No. | PI | Coupler | L* | a* | b* | Color Description |
|---|---|---|---|---|---|---|
| 12 | 3 | 3-Methyl-1-phenyl-2-pyrazolin-5-one | 28.01 | 12.76 | −4.49 | Blue violet |
| 13 | PPD | 2-Methyl-5-aminophenol | 21.60 | 12.13 | −0.79 | Intense violet |

TABLE 3

Dyeing Composition of Reddish Brown Shade on Piedmont Hair

| | Composition (%) |
|---|---|
| Cocamidopropyl betaine | 17.000 |
| Ethanolamine | 2.000 |
| Oleic Acid | 0.750 |
| Citric Acid | 0.100 |
| Ammonium hydroxide | 5.000 |
| Behentrimonium chloride | 0.500 |
| Sodium sulfite | 0.100 |
| EDTA | 0.100 |
| Erythorbic acid | 0.400 |
| Primary intermediate 1 sulfate salt | 0.725 |
| p-Aminophenol | 0.545 |
| 3-Methyl-1-phenyl-2-pyrazolin-5-one | 0.440 |
| 2-Methyl-5-aminophenol | 0.615 |
| Water | QS 100.000 |
| Shade | Reddish Brown |

3. Wash and Light Fastness Testing

Blended gray (50%) was used for the following experiments. For comparative purposes, N,N-bis(2-hydroxyethyl)-p-phenylenediamine 3 which is a common dye ingredient in commercial products was tested as a standard.

To test the degree of resistance to shampoo washing, the colored hair was immersed and shaken for 3 hours in a 10% Herbal Essences solution. Light fastness was tested by subjecting dyed hair to fade-o-meter for 72 hours.

TABLE 4

Tristimulus Value of Shampoo and Light Fastness Studies with 3-aminophenol

| | | Before | | | After | | | |
|---|---|---|---|---|---|---|---|---|
| 3-Aminophenol | PI | L* | a* | b* | L* | a* | b* | ΔE |
| Wash 5 hr | 1 | 16.83 | −0.01 | −2.18 | 17.19 | 0.04 | −1.63 | 0.66 |
| | 2 | 15.21 | 0.06 | −1.17 | 16.03 | 0.04 | −1.20 | 0.82 |
| | 3 | 16.65 | 0.01 | −1.89 | 18.33 | −0.17 | −1.53 | 1.73 |
| Light 72 hour | 1 | 16.83 | −0.01 | −2.18 | 18.17 | −0.14 | −0.15 | 2.44 |
| | 2 | 15.21 | 0.06 | −1.17 | 15.58 | −0.03 | −0.19 | 1.05 |
| | 3 | 16.65 | 0.01 | 1.89 | 18.54 | −0.02 | −0.39 | 2.41 |

TABLE 5

Tristimulus Value of Shampoo and Light Fastness Studies with Blue Coupler 2,4-Diaminophenoxy ethanol on Gray Hair

| | | Before | | | After | | | |
|---|---|---|---|---|---|---|---|---|
| 3-Aminophenol | PI | L* | a* | b* | L* | a* | b* | ΔE |
| Wash 5 hr | 1 | 15.44 | 0.84 | −3.12 | 17.36 | 0.39 | −3.94 | 2.14 |
| | 2 | 15.41 | 0.64 | −2.08 | 17.12 | 0.79 | −3.72 | 2.37 |

TABLE 5-continued

Tristimulus Value of Shampoo and Light Fastness Studies with Blue Coupler 2,4-Diaminophenoxy ethanol on Gray Hair

| | | Before | | | After | | | |
|---|---|---|---|---|---|---|---|---|
| 3-Aminophenol | PI | L* | a* | b* | L* | a* | b* | ΔE |
| | 3 | 15.11 | 0.71 | −3.11 | 18.70 | −0.23 | −4.89 | 4.12 |
| Light 72 hour | 1 | 15.44 | 0.84 | −3.12 | 15.59 | −0.17 | −1.94 | 1.56 |
| | 2 | 15.41 | 0.64 | −2.08 | 15.67 | −0.41 | −1.19 | 1.40 |
| | 3 | 15.11 | 0.71 | −3.11 | 16.51 | −0.43 | −2.03 | 2.10 |

Results of the experiments are summarized in the following tables 4 and 5. ΔE is defined as $$\sqrt{(\Delta L^*)^2 + (\Delta a^*)^2 + (\Delta b^*)^2}$$

and indicates the size of the color difference. The smaller the ΔE value, the better the wash and light fastness.

When coupled with 3-aminophenol, the compound 1 shows better wash fastness property than the compound 3. Total color change (ΔE) of the compound 1 is 0.66, while the compound 3 has ΔE 1.73. Light fastness of 1 is comparable to that of the compound 3 (see Table 4, ΔE: 2.44 vs. 2.41). In the case of blue coupler, 2,4-diamionphenoxyethanol, the compound 1 exhibits better wash and light fastness than the compound 3 (see Table 5).

The contents of all patents, patent applications, published articles; books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. In a composition for the oxidative coloring of hair, said composition consisting essentially of at least one primary dye intermediate and at least one coupling compound in a cosmetically acceptable vehicle, said primary dye intermediate and said coupling compound forming an oxidative hair dye product in the presence of an oxidizing agent, the improvement in which the primary dye intermediate is 1-(4-aminophenyl)-2-pyrrolidinemethanol, or a cosmetically acceptable salt thereof, having formula I:

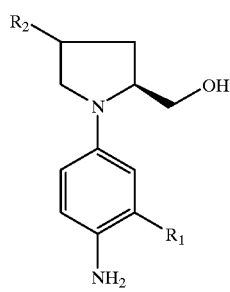

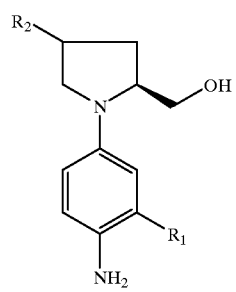

or a cosmetically acceptable salt thereof wherein $R_1$ is hydrogen, $C_1$–$C_6$ alkyl or $C_1$–$C_5$ mono or polyhydroxyalkyl, and $R_2$ is H or OH.

2. The composition according to claim 1, wherein $R_1$ is hydrogen, $C_1$–$C_4$ alkyl or $C_1$–$C_3$ mono- or polyhydroxyalkyl and $R_2$ is hydrogen or hydroxyl.

3. The composition according to claim 2, wherein $R_1$ is hydrogen, methyl or ethyl.

4. The composition according to claim 3, wherein $R_2$ is hydrogen.

5. The composition according to claim 4, wherein $R_1$ is hydrogen.

6. The composition according to claim 1, wherein said 1-(4-aminophenyl)-2-pyrrolidinemethanol primary intermediate is present in an amount of about 0.01% to about 10%, by weight, based on total weight of the composition.

7. The composition according to claim 1, wherein said 1-(4-aminophenyl)-2-pyrrolidinemethanol primary intermediate is present at about 0.1% to about 5%, by weight, based on the total weight of the composition.

8. The composition according to claim 1, further consisting essentially of one or more additional primary intermediates selected from the group consisting of p-phenylenediamine and cosmetically acceptable derivatives thereof; p-aminophenols and cosmetically acceptable derivatives thereof; ortho developers and cosmetically acceptable derivatives thereof, and heterocyclic primary intermediates; and wherein the coupling compound is selected from the group consisting of phenols and cosmetically acceptable derivatives thereof; resorcinols and cosmetically acceptable derivatives thereof; m-phenylenediamines and cosmetically acceptable derivatives thereof; m-aminophenols and cosmetically acceptable derivatives thereof; and heterocyclic coupling compounds.

9. The composition according to claim 1, wherein said coupling compound is selected from the group consisting of 3-aminophenol, resorcinol, 2-methylresorcinol, 2-hydroxy-4-aminotoluene, 1-naphthol, 2-methyl-1-naphthol, 2-(2,4-diaminophenoxy)ethanol and mixtures thereof.

10. The composition according to claim 1, further consisting essentially of an oxidizing agent, whereby said oxidative hair dye product is produced.

11. The composition according to claim 10, wherein said oxidizing agent is hydrogen peroxide.

12. A method for the oxidative coloring of human hair comprising contacting the hair with a hair coloring effective amount of the composition according to claim 1 and maintaining contact with the hair until the hair is colored.

13. An oxidative hair dye product produced by reacting, in a cosmetically acceptable vehicle and in the presence of an oxidizing agent suitable for the oxidative dyeing of hair, a coupling compound and a 1-(4-aminophenyl)-2-pyrrolidine methanol, or a cosmetically acceptable salt thereof, having the formula (I):

wherein $R_1$ is hydrogen, $C_1$–$C_6$ alkyl or $C_1$–$C_5$ mono or polyhydroxyalkyl and $R_2$ is hydrogen or hydroxyl.

14. The hair dye product according to claim 13, wherein $R_1$ is hydrogen, $C_1$–$C_4$ alkyl or $C_1$–$C_3$ mono- or polyhydroxyalkyl and $R_2$ is hydrogen or hydroxyl.

15. The hair dye product according to claim 13, wherein $R_1$ is hydrogen, methyl, ethyl, or $C_1$–$C_3$ monohydroxyalkyl.

16. The hair dye product according to claim 14, wherein $R_1$ is hydrogen.

17. The hair dye product according to claim 14, wherein $R_1$ is methyl.

18. The hair dye product according to claim 13, wherein said coupling compound is selected from the group consisting of 3-aminophenol, 2-hydroxy-4-aminotoluene, resorcinol, 2-methylresorcinol, 1-naphthol, 2-methyl-1-naphthol, 2-(2,4-diaminophenoxy) ethanol and mixtures thereof.

19. The hair dye product of claim 13, wherein the hair dye product is obtained by reacting equimolar amounts of the compound of formula I and the coupling compound.

20. A method of dyeing hair comprising contacting the hair with a hair dye product obtained from the reaction of a primary intermediate and a coupling compound with an oxidant suitable for the oxidative dyeing of hair in an amount sufficient to form said oxidative hair dye product, the primary intermediate being a 1-(4-aminophenyl)-2-pyrrolidinemethanol or a cosmetically acceptable salt thereof having the formula I:

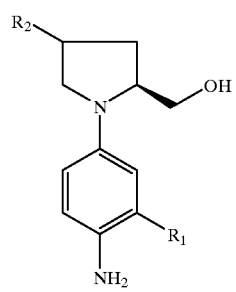

wherein $R_1$ is hydrogen, $C_1$–$C_4$ alkyl or $C_1$–$C_3$ mono- or polyhydroxyalkyl and $R_2$ is H or OH.

21. The method according to claim 20, wherein $R_1$ is hydrogen, methyl or ethyl and $R_2$ is hydrogen.

22. The method according to claim 20 wherein the hair dye composition further comprises additional primary intermediates selected from the group consisting of p-phenylenediamine, p-toluenediamine, N,N-bis (hydroxyethyl)-p-phenylenediamine, 2-hydroxyethyl-p-phenylenediamine, p-aminophenol, 2-methyl-p-aminophenol, 3-methyl-p-aminophenol 2-(2- hydroxyethylamino methyl)-p-aminophenol, p-methylaminophenol 2-methoxymethyl-p-aminophenol, o-aminophenol, 2,4-diaminophenol, 5-methyl-o-aminophenol, 6-methyl-o-aminophenol, and mixtures thereof.

23. The method according to claim 20, wherein said coupling compound is selected from the group consisting of 3-aminophenol, resorcinol, 2-methylresorcinol, 2-hydroxy4-aminotoluene, 1-naphthol, 2-methyl-1-naphthol, 2-(2,4-diaminophenoxy)ethanol, and mixtures thereof.

24. The method according to claim 20, wherein said coupling compound is selected from the group consisting of 3-aminophenol, resorcinol, 2-methylresorcinol, 2-hydroxy-4-aminotoluene, 1-naphthol, 2-methyl-1-naphthol, 2-(2,4-diaminophenoxy)ethanol, and mixtures thereof.

25. The method of claim 23 wherein the total quantity of primary intermediates and coupling compound present in the hair dye composition is from about 0.1 to about 10% by weight of the hair dye composition.

* * * * *